US011236146B2

(12) United States Patent
Lee et al.

(10) Patent No.: US 11,236,146 B2
(45) Date of Patent: Feb. 1, 2022

(54) STABLE PHARMACEUTICAL FORMULATION

(71) Applicant: CELLTRION INC., Incheon (KR)

(72) Inventors: Joon Won Lee, Incheon (KR); Won Yong Han, Incheon (KR); Su Jung Kim, Incheon (KR); Jun Seok Oh, Incheon (KR); So Young Kim, Incheon (KR); Kwang Woo Kim, Incheon (KR); Yeon Kyeong Shin, Incheon (KR)

(73) Assignee: Celltrion Inc., Incheon (KR)

( * ) Notice: Subject to any disclaimer, the term of this patent is extended or adjusted under 35 U.S.C. 154(b) by 90 days.

(21) Appl. No.: 16/345,453

(22) PCT Filed: Oct. 26, 2017

(86) PCT No.: PCT/KR2017/011909
§ 371 (c)(1),
(2) Date: Apr. 26, 2019

(87) PCT Pub. No.: WO2018/080196
PCT Pub. Date: May 3, 2018

(65) Prior Publication Data
US 2019/0248871 A1  Aug. 15, 2019

(30) Foreign Application Priority Data
Oct. 28, 2016  (KR) .................. 10-2016-0142184

(51) Int. Cl.
| | |
|---|---|
| *A61K 39/395* | (2006.01) |
| *C07K 14/705* | (2006.01) |
| *A61K 9/08* | (2006.01) |
| *A61K 47/02* | (2006.01) |
| *A61K 47/18* | (2017.01) |
| *A61K 47/26* | (2006.01) |
| *A61K 47/12* | (2006.01) |
| *A61K 38/16* | (2006.01) |
| *A61K 38/19* | (2006.01) |
| *A61K 38/17* | (2006.01) |

(52) U.S. Cl.
CPC .......... *C07K 14/70578* (2013.01); *A61K 9/08* (2013.01); *A61K 38/16* (2013.01); *A61K 38/1774* (2013.01); *A61K 38/191* (2013.01); *A61K 39/39591* (2013.01); *A61K 47/02* (2013.01); *A61K 47/12* (2013.01); *A61K 47/183* (2013.01); *A61K 47/26* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 4,362,661 A | 12/1982 | Ono et al. | |
| 5,945,098 A | 8/1999 | Sarno et al. | |
| 7,276,477 B2 | 10/2007 | Osslund et al. | |
| 7,648,702 B2 | 1/2010 | Gombotz et al. | |
| 8,008,453 B2 * | 8/2011 | Gegg ..................... | A61K 47/68 530/391.7 |
| 9,453,067 B2 | 9/2016 | Deutel et al. | |
| 9,474,803 B2 | 10/2016 | Park et al. | |
| 10,258,689 B2 | 4/2019 | Choi et al. | |
| 2013/0101583 A1 | 4/2013 | Manning et al. | |
| 2013/0101584 A1 | 4/2013 | Manning et al. | |
| 2014/0186361 A1 * | 7/2014 | Manning ................ | A61P 19/02 424/142.1 |
| 2016/0106844 A1 | 4/2016 | Banado et al. | |

FOREIGN PATENT DOCUMENTS

WO  WO-2013164837 A1 * 11/2013 ............... A61K 9/19

OTHER PUBLICATIONS

International Search Report issued in PCT/KR2017/011909, dated Feb. 14, 2018.
Kamerzell et al., "Protein-excipient interactions: Mechanisms and biophysical characterization applied to protein formulation development" Advanced Drug Delivery Reviews, vol. 63, 2011, pp. 1118-1159.
Ishikawa et al., "Influence of pH on Heat-Induced Aggregation and Degradation of Therapeutic Monoclonal Antibodies" Biol. Pharm. Bull., vol. 33, No. 8, Aug. 2010, pp. 1413-1417.
Extended Search Report issued in European Application No. 17863573. 6, dated Oct. 31, 2019.

* cited by examiner

*Primary Examiner* — Yunsoo Kim
(74) *Attorney, Agent, or Firm* — BakerHostetler

(57) ABSTRACT

Disclosed is a stable pharmaceutical formulation, comprising a fusion protein in which the extracellular ligand-binding domain of a human p75 tumor necrosis factor receptor is fused to the Fc domain of human IgG and a succinate buffering agent, without comprising a stabilizer. The stable pharmaceutical formulation enables the long-term storage of the TNFR-Fc fusion protein formulation and can exhibit superior storage stability without the need for demanding storage conditions, and is a simple formulation because no stabilizer is comprised therein and is thus more economical than other stabilizer-comprising formulations.

13 Claims, No Drawings
Specification includes a Sequence Listing.

SEQUENCE LISTING

```
<160> NUMBER OF SEQ ID NOS: 2

<210> SEQ ID NO 1
<211> LENGTH: 467
<212> TYPE: PRT
<213> ORGANISM: Artificial Sequence
<220> FEATURE:
<223> OTHER INFORMATION: TNFR-Fc

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asp Thr Thr Ser Ser Thr Asp Ile Cys Arg Pro His
145                 150                 155                 160

Gln Ile Cys Asn Val Val Ala Ile Pro Gly Asp Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255
```

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asp Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 2
<211> LENGTH: 235
<212> TYPE: PRT
<213> ORGANISM: Artificial Sequence
<220> FEATURE:
<223> OTHER INFORMATION: TNFR-Fc_TNF-alpha binding domain

<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
                35                  40                  45

Ser Asp Thr Val Cys Asp Ser Cys Glu Asp Ser Thr Tyr Thr Gln Leu
            50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
                130                 135                 140

```
Gly Thr Phe Ser Asp Thr Thr Ser Ser Thr Asp Ile Cys Arg Pro His
145                 150                 155                 160

Gln Ile Cys Asn Val Val Ala Ile Pro Gly Asp Ala Ser Met Asp Ala
                165             170                 175

Val Cys Thr Ser Thr Ser Pro Thr Arg Ser Met Ala Pro Gly Ala Val
            180             185                 190

His Leu Pro Gln Pro Val Ser Thr Arg Ser Gln His Thr Gln Pro Thr
        195             200                 205

Pro Glu Pro Ser Thr Ala Pro Ser Thr Ser Phe Leu Leu Pro Met Gly
    210             215                 220

Pro Ser Pro Pro Ala Glu Gly Ser Thr Gly Asp
225                 230             235
```

STABLE PHARMACEUTICAL FORMULATION

CROSS-REFERENCE TO RELATED APPLICATIONS

The present application is a National Stage of International Patent Application No. PCT/KR2017/011909, filed on Oct. 26, 2017, and claims benefit of Korean Patent Application No. 10-2016-0142184, filed on Oct. 28, 2016, the contents of which are hereby incorporated by reference in their entirety.

BACKGROUND OF THE INVENTION

1. Technical Field

The present invention relates to a stable pharmaceutical formulation.

2. Description of the Related Art

Prepared by fusing the extracellular ligand-binding domain of a human p75 tumor necrosis factor receptor (TNFR) to the Fc domain of human IgG1, a TNFR-Fc fusion protein comprises etanercept. Etanercept comprises 467 amino acids and has an apparent molecular weight of about 150 kDa. It was commercialized with the trade name "Enbrel" by Amgen Inc. in 2002. Etanercept, serving as a TNF-α inhibitor, has been utilized in the treatment of rheumatoid arthritis, psoriasis, ankylosing spondylitis, and the like, and clinical research into applications thereof to vasculitis, Alzheimer's disease and Crohn's disease is ongoing.

In general, antibody drugs, as well as protein drugs, contain active ingredients having very short half-lives and easily undergo chemical and physical denaturation due to inappropriate temperature, shear stress, vibration, freeze-thawing, UV exposure, excessive changes in pH, organic solvents and microbial contamination. Chemical denaturation comprises dimer dissociation, oxidation, deamidation, isomerization and multimerization, which are affected by the amino acid composition of the antibody and the conditions (salt, pH and temperature) of the solvent containing the antibody. Physical denaturation comprises loss of tertiary structures, and monomer covalent/non-covalent aggregation and adsorption, which are affected by hydrophobic patches on the protein surface altered by the antibody-containing surrounding environments, such as solvents, complex protein structures, such as charge distribution, and thermal stability.

The physical or chemical denaturation of a protein comprising an antibody entails the loss of the physiological activity thereof. Furthermore, since such denaturation is irreversible, it is difficult to restore the original properties of the denatured antibody, thus deteriorating therapeutic efficacy. Moreover, it has been reported that phenomena such as aggregation of monomers cause an immune response, and thorough research into the formulation in a physiologically effective amount without such aggregation has been conducted (Ishikawa et al., Biol. Pharm. Bull., 33(8): 1413-1417, 2010).

Accordingly, many methods have been studied in order to prevent the denaturation of antibody drugs, and attempts have been made to add an excipient or to adjust pH or buffer composition. In the case where aggregation occurs by exposing the hydrophobic groups of the antibody protein to the surface of the molecule to thus bind them to each other, a method capable of stabilizing the exposed hydrophobic groups is utilized as an excipient for preventing aggregation. There are, for example, amino acids, such as arginine, lysine, proline, histidine, glycine and the like (U.S. Pat. Nos. 4,362,661, 7,648,702), polysorbate-based surfactants, amphiphilic polymers such as polyethylene glycol (PEG) or polyvinyl pyrrolidone (PVP), polysaccharides such as dextran, and monosaccharides or disaccharides such as sucrose, maltose, trehalose and the like (U.S. Pat. No. 5,945,098A).

Although a variety of stabilizers have been studied to prepare a protein drug stabilization formulation, there is a need for stabilizers suitable for the physical and chemical properties of individual active ingredients. If the concentration control of the stabilizer fails, there is difficulty, such as adverse effects different from desired effects of the drug, attributable to the side effects between the stabilizer and the drug. Furthermore, when an amino acid is added as the stabilizer, denaturation may easily occur due to heat, which is undesirable. In the case where certain saccharides produce impurities or reducing sugars while degrading during storage, glycation may take place, adversely affecting protein stability. When a surfactant decomposes due to external environmental conditions during storage, a peroxide may be formed, and may serve as a factor that oxidizes proteins (Kamerzell, Tim. J., et al. Advanced drug delivery reviews 63.13 (2011): 1118-1159.).

U.S. Pat. No. 7,648,702 discloses a pharmaceutical composition comprising etanercept and 10-200 mM L-arginine. However, the phosphate buffer contained in the pharmaceutical composition has insufficient stabilization effects in terms of aggregate formation, and sucrose promotes the formation of polymer impurities, which may adversely affect protein stability.

Korean Patent No. 10-1482304 discloses an etanercept solution formulation comprising etanercept and 0.1~250 mM of at least one stabilizer selected from the group consisting of methionine, lysine, histidine, and pharmaceutically acceptable salts thereof. However, the phosphate buffer contained in the etanercept formulation has insufficient stability effects, and histidine contained as the stabilizer may form polymer impurities, which may cause problems of protein stability.

Korean Patent No. 10-1419884 discloses a composition for the treatment of arthritis, comprising etanercept, an ammonium salt and a succinate. However, the etanercept-containing composition may incur potential problems in terms of safety because, with the exception of ammonium sulfate, the ammonium salts such as ammonium chloride, ammonium carbonate, and ammonium nitrate are not approved as excipients for injection by the U.S. Food and Drug Administration (FDA).

Korean Patent Application Publication No. 2014-0027274 discloses a pharmaceutical composition, comprising etanercept, a citrate buffering agent, and an amino acid selected from the group consisting of lysine, proline and pharmaceutically acceptable salts thereof, in which the citrate buffering agent has a concentration of 25 mM to 120 mM and the amino acid has a concentration of 15 mM to 100 mM. However, in the case where citrate contained in the etanercept formulation is used as the buffer, the effect of inhibition of protein oxidation is insufficient and pain may occur upon injection.

Therefore, the present inventors have studied pharmaceutical formulations that are able to stably maintain the activity of TNFR-Fc fusion protein without the stabilizer and thus have ascertained that a formulation comprising a succinate buffer is very effective at stabilizing the TNFR-Fc fusion protein even without any stabilizer, which culminates in the present invention.

SUMMARY OF THE INVENTION

Accordingly, the present invention is intended to provide a stable pharmaceutical formulation, which comprises a TNFR-Fc fusion protein and a succinate buffering agent, without comprising a stabilizer.

In addition, the present invention is intended to provide a stable pharmaceutical formulation, which comprises a TNFR-Fc fusion protein, a succinate buffering agent and an isotonic agent at predetermined concentrations, without comprising a stabilizer.

In addition, the present invention is intended to provide a stable pharmaceutical formulation for subcutaneous administration, which comprises a TNFR-Fc fusion protein, a succinate buffering agent and an isotonic agent at predetermined concentrations, without comprising a stabilizer.

In order to achieve the above object, the present invention provides a stable pharmaceutical formulation, comprising a fusion protein in which the extracellular ligand-binding domain of a human p75 tumor necrosis factor receptor is fused to the Fc domain of human IgG and a succinate buffering agent, without comprising a stabilizer.

The present invention provides a stable pharmaceutical formulation, comprising a fusion protein in which the extracellular ligand-binding domain of a human p75 tumor necrosis factor receptor is fused to the Fc domain of human IgG and a succinate buffering agent, without comprising an amino acid, an ammonium salt, a saccharide or a mixture thereof as a stabilizer.

In an embodiment of the present invention, the fusion protein may comprise the amino acid sequence of SEQ ID NO:1.

In an embodiment of the present invention, the fusion protein may comprise the amino acid sequence of SEQ ID NO:2.

In an embodiment of the present invention, the fusion protein may be comprised at a concentration of 1 to 100 mg/mL.

In an embodiment of the present invention, the succinate buffering agent may comprise a succinate at a concentration of 1 to 200 mM.

In an embodiment of the present invention, the stable pharmaceutical formulation of the present invention may further comprise an isotonic agent.

In an embodiment of the present invention, the isotonic agent may be sodium chloride at a concentration of 1 to 1000 mM.

In an embodiment of the present invention, the pH of the stable pharmaceutical formulation may range from 5.5 to 6.5.

In an embodiment of the present invention, the ammonium salt may be ammonium chloride, ammonium sulfate, ammonium carbonate, ammonium nitrate or a mixture thereof.

In an embodiment of the present invention, the amino acid may be arginine, methionine, lysine, histidine, glycine, proline, alanine, valine, isoleucine, leucine, phenylalanine, tyrosine, tryptophan, cysteine, aspartic acid, glutamic acid, serine, asparagine, threonine, glutamine or a mixture thereof.

In an embodiment of the present invention, the saccharide may be sucrose.

In an embodiment of the present invention, the stable pharmaceutical formulation may comprise 12% or less of a high-molecular-weight component as measured using size-exclusion high-performance liquid chromatography (SE-HPLC) after storage at 40° C.±2° C. for 12 weeks.

In an embodiment of the present invention, the stable pharmaceutical formulation may comprise 24% or less of a high-molecular-weight component as measured using hydrophobic-interaction high-performance liquid chromatography (HI-HPLC) after storage at 40° C.±2° C. for 12 weeks.

In an embodiment of the present invention, the stable pharmaceutical formulation may comprise a 1~100 mg/mL fusion protein comprising the amino acid sequence of SEQ ID NO:2, a 1~200 mM succinate buffer, and 1~1000 mM sodium chloride, without comprising a stabilizer, in which the concentrations of the succinate buffer and the sodium chloride are adjusted in the osmotic pressure range of 200 to 400 mOsm of the formulation.

The stable pharmaceutical formulation of the present invention may comprise a 45~55 mg/mL fusion protein comprising the amino acid sequence of SEQ ID NO:2, a 5~45 mM succinate buffer, and 100 mM or more of sodium chloride, without comprising a stabilizer.

According to the present invention, a stable pharmaceutical formulation comprising no stabilizer enables the long-term storage of a TNFR-Fc fusion protein formulation and can exhibit excellent storage stability without the need for demanding storage conditions. The formulation of the present invention is a simple formulation because no stabilizer is contained therein, and is thus more economical than other stabilizer-containing formulations.

DESCRIPTION OF THE SPECIFIC EMBODIMENTS

[Stable Pharmaceutical Formulation]

According to the present invention, a stable pharmaceutical formulation comprises a fusion protein in which the extracellular ligand-binding domain of a human p75 tumor necrosis factor receptor is fused to the Fc domain of human IgG and a succinate buffering agent, without comprising a stabilizer.

According to the present invention, a stable pharmaceutical formulation comprises a fusion protein in which the extracellular ligand-binding domain of a human p75 tumor necrosis factor receptor is fused to the Fc domain of human IgG and a succinate buffering agent, without comprising an amino acid, an ammonium salt, a saccharide or a mixture thereof as a stabilizer.

In an embodiment of the present invention, the stable pharmaceutical formulation of the present invention may further comprise an additive that is known in the art within a range that does not substantially adversely affect the activity of an antibody or the stability of a formulation and low viscosity thereof. For example, an aqueous carrier, an antioxidant, or a mixture of two or more thereof may be further comprised. The aqueous carrier is a carrier that is pharmaceutically acceptable (safe and nontoxic upon administration to humans) and is useful for the preparation of a pharmaceutical formulation. Examples of the aqueous carrier may comprise, but are not limited to, sterile water for injection (SWFI), bacteriostatic water for injection (BWFI), a sterile saline solution, Ringer's solution, dextrose, and the like. Examples of the antioxidant may comprise, but are not limited to, ascorbic acid and the like.

As used herein, the expression "without comprising" or "comprises no" means that absolutely none of the corresponding component is comprised. Also, the above expression means that the corresponding component is not substantially comprised, namely is comprised within a range that does not affect the activity of an antibody or the stability of a pharmaceutical formulation, in an amount of, for example, 0 to 1% (w/v), 0 to 1 ppm (w/v) or 0 to 1 ppb (w/v), based on the total weight of the pharmaceutical formulation.

(A) Fusion Protein

In an embodiment of the present invention, the fusion protein in which the extracellular ligand-binding domain of a human p75 tumor necrosis factor receptor is fused to the Fc domain of human IgG may comprise the amino acid sequence of SEQ ID NO:1. In an embodiment of the present invention, the fusion protein may comprise the amino acid sequence of SEQ ID NO:2.

In an embodiment of the present invention, the fusion protein may be a modified fusion protein, obtained by subjecting the amino acid sequence of SEQ ID NO:2 to amino acid substitution, deletion or insertion, or may be a peptide analogue having activity similar to that of etanercept.

In the present invention, the concentration of the fusion protein may be freely adjusted within a range that does not substantially adversely affect the stability of the stable pharmaceutical formulation of the present invention.

In an embodiment of the present invention, the concentration of the TNFR-Fc fusion protein is 1 mg/mL or more. In another embodiment, the concentration of the TNFR-Fc fusion protein may be 1 to 100 mg/mL. In still another embodiment, the concentration of the TNFR-Fc fusion protein may be 20 to 80 mg/mL. In yet another embodiment, the concentration of the TNFR-Fc fusion protein may be 40 to 60 mg/mL. In still yet another embodiment, the concentration of the TNFR-Fc fusion protein may be 50 mg/mL. When the concentration of the TNFR-Fc fusion protein falls within the above range, the free selection of administration dose and period may increase depending on the amount of the fusion protein, and long-term stability may be improved.

Also, the stable pharmaceutical formulation of the present invention exhibits superior stabilization effects in 'fusion protein', rather than in 'antibody' such as infliximab, trastuzumab or eculizumab.

(B) Succinate Buffer

Examples of the succinate buffer may comprise, but are not limited to, sodium succinate, zinc succinate, aluminum succinate, potassium succinate, and the like. The succinate buffer may be prepared by mixing the succinate with succinic acid.

In an embodiment of the present invention, the succinate buffer may comprise sodium succinate.

In an embodiment of the present invention, the amount of succinate in the succinate buffer may be freely adjusted within a range that does not substantially adversely affect the stability of the pharmaceutical formulation according to the present invention. For example, the amount of succinate in the succinate buffer may range from 1 to 200 mM. In another embodiment of the present invention, the amount of succinate may range from 3 to 100 mM. In still another embodiment, the amount of succinate may range from 5 to 45 mM. In yet another embodiment, the amount of succinate may range from 15 to 35 mM. In still yet another embodiment, the amount of succinate may range from 5 to 24 mM. When the amount of succinate falls within the above range, superior long-term stability may be exhibited. If the amount of succinate is less than 1 mM, the action as the buffer may be inefficient. On the other hand, if the amount thereof exceeds 200 mM, the resulting formulation may be increased in viscosity and may thus be unsuitable for use.

The amount of succinate may be a succinate content in the formulation stored in a single container. In a container for multiple distributions or multiple administrations, the amount of succinate may be increased several times depending on the number of distributions or administrations. In contrast, when a small container is used, the amount of succinate may be decreased so as to be suitable therefor.

(C) Stabilizer

According to the present invention, the stable pharmaceutical formulation comprises no stabilizer, and the stabilizer that is not comprised may be an amino acid, an ammonium salt, a saccharide or a mixture thereof in an embodiment of the present invention.

In an embodiment of the present invention, the ammonium salt that is not comprised may be, but is not limited to, ammonium chloride, ammonium sulfate, ammonium carbonate, ammonium nitrate or mixtures thereof. Ammonium salts other than ammonium sulfate are not registered in the Inactive Ingredient Database (IID) of the excipient database of drugs approved for human administration by U.S. FDA and are thus unsuitable for use for administration via injection into the human body (www.fda.gov).

In an embodiment of the present invention, the amino acid that is not comprised may be, but is not limited to, arginine, methionine, lysine, histidine, glycine, proline, alanine, valine, isoleucine, leucine, phenylalanine, tyrosine, tryptophan, cysteine, aspartic acid, glutamic acid, serine, asparagine, threonine, glutamine or mixtures thereof.

In an embodiment of the present invention, the saccharide that is not comprised may be, but is not limited to, sucrose.

In an embodiment of the present invention, the stabilizer that is not comprised may be a surfactant, and the surfactant may be, but is not limited to, polysorbate 20, polysorbate 80, poloxamer or mixtures thereof.

In an embodiment of the present invention, the stabilizer that is not comprised may be a polymer, examples of which may comprise, but are not limited to, polyethylene glycol, polyvinyl pyrrolidone, carboxymethylcellulose, hyaluronic acid, cyclodextrin, and mixtures thereof.

In an embodiment of the present invention, the stabilizer that is not comprised may be a saccharide, examples of the saccharide being, but not being limited to, polysaccharides such as dextran, sucrose, maltose, trehalose, and mixtures thereof.

(D) Isotonic Agent

The stable pharmaceutical formulation according to the present invention may comprise an isotonic agent, and examples of the isotonic agent may comprise, but are not limited to, sodium chloride, potassium chloride, boric acid, sodium borate, and mixtures thereof.

In an embodiment of the present invention, these isotonic agents may be used alone or in combinations of two or more. In another embodiment of the present invention, the isotonic agent may function to maintain the osmotic pressure of the formulation at 200 to 400 mOsm.

In an embodiment of the present invention, the isotonic agent may be sodium chloride. The amount of the isotonic agent may be freely adjusted within a range that does not substantially adversely affect the stability of the pharmaceutical formulation according to the present invention. The amount of the isotonic agent falls in the range of 1 to 1000 mM. In another embodiment of the present invention, the amount of the isotonic agent may range from 50 to 800 mM. In still another embodiment, the amount of the isotonic agent may range from 80 to 700 mM. In yet another embodiment, the amount of the isotonic agent may range from 90 to 600 mM. In still yet another embodiment, the amount of the isotonic agent may range from 100 to 500 mM. In even still yet another embodiment, the amount of the isotonic agent may range from 110 to 400 mM. In a further embodiment, the amount of the isotonic agent may range from 115 to 300 mM. In still a further embodiment, the amount of the isotonic agent may range from 120 to 200 mM. In yet a further embodiment, the amount of the isotonic agent may range from 120 to 180 mM. In still yet a further embodiment, the amount of the isotonic agent may range from 120 to 160 mM. In even still yet a further embodiment, the amount of the isotonic agent may range from 130 to 150 mM.

(E) pH

The pH of the pharmaceutical formulation according to the present invention may be adjusted to fall within the range of 5.5 to 6.5. In an embodiment of the present invention, the pH of the pharmaceutical formulation ranges from 5.7 to 6.3. In an embodiment of the present invention, the pH of the pharmaceutical formulation ranges from 6.0 to 6.5. In an embodiment of the present invention, the pH of the pharmaceutical formulation ranges from 5.5 to 6.0. In another embodiment, the pH of the pharmaceutical formulation may be adjusted to 6.0. If the pH thereof is less than 5.5 or exceeds 6.5, aggregation of the fusion protein may increasingly occur. Hence, the pH of the pharmaceutical formulation preferably falls within the above range.

(F) "Stable" Pharmaceutical Formulation

In the "stable" pharmaceutical formulation according to the present invention, the term "stable" means that the fusion protein according to the present invention substantially retains physical stability, chemical stability and/or biological activity during the preparation process thereof and/or upon the storage thereof. A variety of analytical techniques for measuring the stability of the fusion protein may be easily performed in the art.

Physical stability may be evaluated through any method known in the art, comprising measurement of a sample's apparent attenuation of light (absorbance or optical density).

Such measurement of light attenuation is related to the turbidity of a formulation. For physical stability, high-molecular-weight component content, low-molecular-weight component content, intact protein content, the number of insoluble foreign particles and the like may be measured.

As used herein, the term "high-molecular-weight component" refers to a peak in which the retention time thereof is located before the main peak (intact fusion protein). Typically, a high-molecular-weight component is a complex having a molecular weight greater than that of the TNFR-Fc fusion protein in the form of a therapeutic monomer, for example, a molecular weight exceeding about 150 kDa.

As used herein, the term "low-molecular-weight component" refers to a peak in which the retention time thereof is located after the main peak (intact fusion protein). Typically, a low-molecular-weight product is a complex having a molecular weight lower than that of the therapeutic TNFR-Fc fusion protein, for example, a molecular weight of less than about 150 kDa.

Chemical stability may be evaluated by, for example, detecting and quantifying the antibody in the chemically modified form. Chemical stability comprises, for example, charge change that may be assessed by ion exchange chromatography (e.g. resulting from deamidation or oxidation). For chemical stability, a charge variant (acidic or basic peak) may be measured.

The biological activity may be evaluated through any method known in the art, comprising, for example, measuring antigen-binding affinity using ELISA.

In an embodiment of the present invention, the pharmaceutical formulation may be stable for a long period of time.

In an embodiment of the present invention, the term "stable" pharmaceutical formulation refers to a pharmaceutical formulation satisfying at least one of the following criteria.

Main Component Content (Main Peak)

A stable pharmaceutical formulation, the main component content of which is measured to be 65% to 100% through SE-HPLC after storage at a temperature of 40° C.±2° C. for 12 weeks.

A stable pharmaceutical formulation, the main component content of which is measured to be 65% to 100% through SE-HPLC after storage at a temperature of 40° C.±2° C. and a relative humidity of 75±5% for 12 weeks.

A stable pharmaceutical formulation, the main component content of which is measured to be 64% to 100% through HI-HPLC after storage at a temperature of 40° C.±2° C. for 12 weeks.

A stable pharmaceutical formulation, the main component content of which is measured to be 64% to 100% through HI-HPLC after storage at a temperature of 40° C.±2° C. and a relative humidity of 75±5% for 12 weeks.

High-Molecular-Weight Component

A stable pharmaceutical formulation, the high-molecular-weight component content of which is measured to be 12% or less through SE-HPLC after storage at a temperature of 40° C.±2° C. for 12 weeks.

A stable pharmaceutical formulation, the high-molecular-weight component content of which is measured to be 12% or less through SE-HPLC after storage at a temperature of 40° C.±2° C. and a relative humidity of 75±5% for 12 weeks.

A stable pharmaceutical formulation, the high-molecular-weight component content of which is measured to be 24% or less through HI-HPLC after storage at a temperature of 40° C.±2° C. for 12 weeks.

A stable pharmaceutical formulation, the high-molecular-weight component content of which is measured to be 24% or less through HI-HPLC after storage at a temperature of 40° C.±2° C. and a relative humidity of 75±5% for 12 weeks.

Oxidation Rate

A pharmaceutical formulation, the oxidation rate of heavy-chain Met 272 of which is measured to be less than 3.0% through LS-MS after storage at a temperature of 40° C.±2° C. for 12 weeks.

A pharmaceutical formulation, the oxidation rate of heavy-chain Met 272 of which is measured to be less than 3.0% through LS-MS after storage at a temperature of 40° C.±2° C. and a relative humidity of 75±5% for 12 weeks.

[Method of Preparing Stable Pharmaceutical Formulation]

The stable pharmaceutical formulation according to the present invention may be prepared using any known method, and is not limited to specific methods. For example, the stable pharmaceutical formulation of the invention may be prepared by mixing a TNFR-Fc fusion protein with a succinate buffer containing no stabilizer and a solution comprising an isotonic agent.

In an embodiment of the present invention, the prepared pharmaceutical formulation of the invention may be placed in an airtight container immediately after processing such as sterile treatment or the like.

[Method of Using Stable Pharmaceutical Formulation]

The stable pharmaceutical formulation of the present invention may be used to treat a disease to which the activity of TNF-α is detrimental. Examples of the disease to which the activity of TNF-α is detrimental may comprise, but are not limited to, sepsis, autoimmune disease, infectious disease, grafting, malignant cancer, lung disorders, intestinal disorders, cardiac disorders, and the like.

The stable pharmaceutical formulation according to the present invention may be used as a therapeutic agent for a disease that may be treated by etanercept. Since etanercept may act as a biological inflammation modulator that plays a role in inhibiting the immune response associated with TNF-α in vivo, the formulation of the present invention may be used for the treatment of rheumatoid arthritis, psoriasis, ankylosing spondylitis, vasculitis, Alzheimer's disease, Crohn's disease, and the like, but is not limited thereto.

The stable pharmaceutical formulation according to the present invention may be administered in vivo through oral administration or parenteral administration such as subcutaneous, intramuscular, intraperitoneal, intrasternal, percutaneous, and intravenous injection and infusion, but is not limited thereto. Preferably the stable pharmaceutical formulation of the present invention is administered in the form of an injection.

The amount and timing of administration of the pharmaceutical formulation of the invention depend on the type of disease, the severity and course of the disease, the patient's health and treatment regime, and the judgment of the treating doctor, and are not limited to specific values. For example, administration in an amount of 25 mg each twice a week or in an amount of 50 mg per week, or administration in an amount of 50 mg each twice a week is performed for 12 weeks (or 3 months), followed by administration in an amount of 25 mg each twice a week or 50 mg per week, 0.4 mg/kg twice a week (the maximum single dose not exceeding 25 mg), or 0.8 mg/kg once a week (the maximum single dose not exceeding 50 mg).

[Treatment Method and Stabilization Method]

The present invention addresses a method of treating a disease to which the activity of TNF-α is detrimental, comprising administering, to a patient suffering from a disease to which the activity of TNF-α is detrimental, a stable pharmaceutical formulation comprising a fusion protein in which the extracellular ligand-binding domain of a human p75 tumor necrosis factor receptor is fused to the Fc domain of human IgG and a succinate buffering agent, without comprising a stabilizer.

In addition, the present invention addresses a stable pharmaceutical formulation comprising a fusion protein in which the extracellular ligand-binding domain of a human p75 tumor necrosis factor receptor is fused to the Fc domain of human IgG and a succinate buffering agent, without comprising an amino acid, an ammonium salt, a saccharide or a mixture thereof as a stabilizer.

In addition, the present invention addresses a method of stabilizing a fusion protein in a pharmaceutical formulation, comprising preparing a stable pharmaceutical formulation comprising a fusion protein in which the extracellular ligand-binding domain of a human p75 tumor necrosis factor receptor is fused to the Fc domain of human IgG and a succinate buffering agent, without comprising a stabilizer.

In an embodiment for the treatment method or the stabilization method, the fusion protein may comprise the amino acid sequence of SEQ ID NO:1.

In an embodiment for the treatment method or the stabilization method, the fusion protein may comprise the amino acid sequence of SEQ ID NO:2.

In an embodiment for the treatment method or the stabilization method, the concentration of the fusion protein may be 1 to 100 mg/mL.

In an embodiment for the treatment method or the stabilization method, the succinate buffering agent may comprise a succinate at a concentration of 1 to 200 mM.

In an embodiment for the treatment method or the stabilization method, the pharmaceutical formulation may further comprise an isotonic agent.

In an embodiment for the treatment method or the stabilization method, the isotonic agent may be sodium chloride at a concentration of 1 to 1000 mM.

In an embodiment for the treatment method or the stabilization method, the pharmaceutical formulation may have a pH of 5.5 to 6.5.

In an embodiment for the treatment method or the stabilization method, the stabilizer may be an amino acid, an ammonium salt, a saccharide or a mixture thereof.

In an embodiment for the treatment method or the stabilization method, the ammonium salt may be ammonium chloride, ammonium sulfate, ammonium carbonate, ammonium nitrate or a mixture thereof.

In an embodiment for the treatment method or the stabilization method, the amino acid may be arginine, methionine, lysine, histidine, glycine, proline, alanine, valine, isoleucine, leucine, phenylalanine, tyrosine, tryptophan, cysteine, aspartic acid, glutamic acid, serine, asparagine, threonine, glutamine or a mixture thereof.

In an embodiment for the treatment method or the stabilization method, the saccharide may be sucrose.

In an embodiment for the treatment method or the stabilization method, the pharmaceutical formulation may comprise 12% or less of a high-molecular-weight component as measured using SE-HPLC after storage at a temperature of 40° C.±2° C. for 12 weeks.

In an embodiment for the treatment method or the stabilization method, the pharmaceutical formulation may comprise 24% or less of a high-molecular-weight component as measured using HI-HPLC after storage at a temperature of 40° C.±2° C. for 12 weeks.

Product

The present invention addresses a product, comprising the stable pharmaceutical formulation and a container that accommodates the stable pharmaceutical formulation in an airtight state.

The stable pharmaceutical formulation is described as above.

In an embodiment of the present invention, the container may be formed of glass, a polymer (plastic), a metal, or the like, but is not limited thereto. In an embodiment of the present invention, the container is a bottle, a vial, a syringe, or a tube, but is not limited thereto. In an embodiment of the present invention, the container may be a vial made of glass or polymer, or a prefilled syringe made of glass or polymer. In an embodiment of the present invention, the inner surface of the container may not be coated with silicone oil. Upon coating with silicone oil, stability may deteriorate. The container may be a single-dose or multi-dose container.

In an embodiment of the present invention, the product may further comprise instructions for either or both of the method of using the stable pharmaceutical formulation and the method of storing the stable pharmaceutical formulation. The usage method comprises cure of a disease to which the activity of TNF-α is detrimental, and may comprise an administration route, dose, and timing.

In an embodiment of the present invention, the product may comprise other tools necessary from the viewpoint of a commercial purpose and a user, such as a needle, an injector, an auto-injector, and the like.

A better understanding of the present invention will be given of the following examples, which are set forth to illustrate, but are not to be construed as limiting the scope of, the present invention.

[Preparation of Test Formulation]

In order to prepare and evaluate the stable formulation optimized for the TNFR-Fc fusion protein, respective formulations of Examples 1 to 8 and Comparative Examples 1 to 3 were prepared as follows.

The formulation of Example 1 at a pH of 6.0 was prepared by adding a TNFR-Fc fusion protein in an amount of 50 mg/mL to a 5 mM succinate solution and then adding 140 mM sodium chloride as an isotonic agent, without the addition of a stabilizer.

The formulations of Examples 2 and 3 at a pH of 6.0 were prepared by adding a TNFR-Fc fusion protein in an amount of 50 mg/mL to a 25 mM succinate solution and then adding 140 mM sodium chloride and 120 mM sodium chloride as respective isotonic agents, without the addition of a stabilizer.

The formulations of Examples 4, 5 and 6 at respective pH of 6.0, 5.5 and 6.5 were prepared by adding a TNFR-Fc fusion protein in an amount of 50 mg/mL to a 10 mM succinate solution and then adding 140 mM sodium chloride as an isotonic agent, without the addition of a stabilizer.

The formulations of Examples 7 and 8 at a pH of 6.0 were prepared by adding a TNFR-Fc fusion protein in an amount of 50 mg/mL to a 10 mM succinate solution and then adding 120 mM sodium chloride and 160 mM sodium chloride as respective isotonic agents, without the addition of a stabilizer.

Also, in order to prepare solutions in the same dosage form as Enbrel product, available from Amgen Inc., U.S.A., the formulation of Comparative Example 1 at a pH of 6.3 was prepared by adding a TNFR-Fc fusion protein in an amount of 50 mg/mL to a 25 mM phosphate solution, and adding 100 mM sodium chloride as an isotonic agent and then adding 1% sucrose and 25 mM arginine as stabilizers.

The formulation of Comparative Example 2 at a pH of 6.0 was prepared by adding a TNFR-Fc fusion protein in an amount of 50 mg/mL to a 25 mM histidine buffer and then adding 140 mM sodium chloride as an isotonic agent.

The formulation of Comparative Example 3 at a pH of 6.0 was prepared by adding a TNFR-Fc fusion protein in an amount of 50 mg/mL to a 10 mM citrate buffer and then adding 140 mM sodium chloride as an isotonic agent.

TABLE 1

| No. | Buffer | pH | NaCl | Stabilizer |
| --- | --- | --- | --- | --- |
| Example 1 | 5 mM Succinate | 6.0 | 140 mM NaCl | — |
| Example 2 | 25 mM Succinate | 6.0 | 140 mM NaCl | — |
| Example 3 | 25 mM Succinate | 6.0 | 120 mM NaCl | — |
| Example 4 | 10 mM Succinate | 6.0 | 140 mM NaCl | — |
| Example 5 | 10 mM Succinate | 5.5 | 140 mM NaCl | — |
| Example 6 | 10 mM Succinate | 6.5 | 140 mM NaCl | — |
| Example 7 | 10 mM Succinate | 6.0 | 120 mM NaCl | — |
| Example 8 | 10 mM Succinate | 6.0 | 160 mM NaCl | — |
| Comparative Example 1 | 25 mM Phosphate | 6.3 | 100 mM NaCl | 1% Sucrose, 25 mM Arginine |
| Comparative Example 2 | 25 mM Histidine | 6.0 | 140 mM NaCl | — |
| Comparative Example 3 | 10 mM Citrate | 6.0 | 140 mM NaCl | — |

Each of the formulations prepared as above was placed in an amount of 1.0 mL in a 1.0 mL glass syringe, sealed, stored under harsh conditions of 40° C. for 12 weeks, and then compared and evaluated for the extents of aggregation and oxidation of the TNFR-Fc fusion protein.

[Analysis Method]

SE-HPLC Analysis

In order to evaluate the stability of the formulations of Examples of Table 1, analysis was performed using SE-HPLC. The extent of aggregation of the TNFR-Fc fusion protein was measured by detecting the protein peak at 214 nm using a TSK-gel column under mobile-phase conditions of phosphate and sodium chloride. The TNFR-Fc fusion protein aggregate was eluted from the column earlier than the main peak, and the peak area of the aggregate relative to the total peak area was calculated, and thus the extent of aggregation was evaluated. The amount of the TNFR-Fc fusion protein, excluding impurities, was represented by the main peak, and the area ratio thereof relative to the total peak area was calculated and evaluated.

HI-HPLC Analysis

The extent of structural change in the TNFR-Fc fusion protein was evaluated using HI-HPLC. The protein peak was detected at 218 nm using a Butyl-NPR column under mobile-phase conditions of ammonium sulfate and phosphate. The main peak indicates the TNFR-Fc fusion protein, the peak eluted earlier than the main peak indicates a low-molecular-weight product associated with the TNFR-Fc fusion protein, and the peak eluted later than the main peak indicates an aggregate associated with the TNFR-Fc fusion protein. The peak area of the aggregate relative to the total peak area was calculated to evaluate the extent of aggregation. Also, the amount of the TNFR-Fc fusion protein, excluding impurities, was represented by the main peak, and the area ratio thereof relative to the total peak area was calculated and evaluated.

Oxidation (M272) Analysis

In order to evaluate the stability effect on the extent of oxidation of the TNFR-Fc fusion protein, peptide mapping analysis was performed using an LC/MS system. A mobile-phase buffer was prepared using formic acid and acetonitrile. For analysis, a C18 column was used, and the peak was detected using an ESI Q-TOF mass spectrometer.

1. Test Example 1: Evaluation of Stability of TNFR-Fc Fusion Protein Solution Formulation Comprising Succinate Buffering Agent, without Comprising Stabilizer (1) SE-HPLC Analysis The amounts of SE-HPLC high-molecular-weight components (aggregates eluted earlier than the main peak) of the succinate formulations comprising no stabilizer (Examples 1 to 4, Examples 7 and 8) and the Enbrel formulation of Amgen Inc. comprising sucrose and arginine stabilizers (Comparative Example 1) are shown in Table 2 below.

TABLE 2

| No. | Time 0 (%) | After 12 weeks (%) |
|---|---|---|
| Example 1 | 0.71 | 11.06 |
| Example 2 | 0.71 | 10.25 |
| Example 3 | 0.73 | 10.35 |
| Example 4 | 0.71 | 10.49 |
| Example 7 | 0.70 | 11.01 |
| Example 8 | 0.69 | 9.75 |
| Comparative Example 1 | 0.73 | 14.07 |

The amounts of aggregates of the succinate formulations comprising no stabilizer (Examples 1 to 4, Examples 7 and 8) were 11.1% or less, whereas the Enbrel formulation comprising sucrose and arginine stabilizers (Comparative Example 1) had an aggregate content of 14.1%.

Compared to the Enbrel formulation of Amgen Inc. comprising sucrose and arginine stabilizers (Comparative Example 1), the succinate formulations comprising no stabilizer (Examples 1 to 4, Examples 7 and 8) exhibited superb stabilization effects in terms of aggregate formation.

Thereby, the succinate formulation comprising no stabilizer manifested excellent stability compared to the stabilizer-comprising phosphate formulation.

(2) HI-HPLC Analysis

The amounts of HI-HPLC high-molecular-weight components (aggregates eluted later than the main peak) of the succinate formulations comprising no stabilizer (Examples 1 to 4, Examples 7 and 8) and the Enbrel formulation of Amgen Inc. comprising sucrose and arginine stabilizers (Comparative Example 1) are shown in Table 3 below.

TABLE 3

| No. | Time 0 (%) | After 12 weeks (%) |
|---|---|---|
| Example 1 | 16.7 | 23.0 |
| Example 2 | 16.6 | 22.8 |
| Example 3 | 16.6 | 23.0 |
| Example 4 | 16.6 | 22.5 |
| Example 7 | 16.5 | 23.3 |
| Example 8 | 16.7 | 22.1 |
| Comparative Example 1 | 16.7 | 25.1 |

The HI-HPLC results of Table 3 were similar to the SE-HPLC results of Table 2. The succinate formulations comprising no stabilizer (Examples 1 to 4, Examples 7 and 8) showed an aggregate content of 23.3% or less, whereas the stabilizer-comprising Enbrel formulation (Comparative Example 1) showed an aggregate content of 25.1%.

Thus, the succinate formulation comprising no stabilizer manifested excellent stability compared to the stabilizer-comprising phosphate formulation.

2. Test Example 2: Evaluation of Stability of TNFR-Fc Fusion Protein Formulation Comprising Succinate Buffering Agent (1) High Stability of Succinate Buffer
1) HI-HPLC Analysis In order to evaluate the importance of the buffer in the stabilization of the TNFR-Fc fusion protein, the succinate buffer formulation (Example 4), the phosphate buffer formulation (Comparative Example 1), the histidine buffer formulation (Comparative Example 2), and the citrate buffer formulation (Comparative Example 3) were stored at 40° C. for 12 weeks, after which the amounts of HI-HPLC high-molecular-weight components (aggregates eluted later than the main peak) thereof were analyzed. The results are shown in Table 4 below.

TABLE 4

| No. | Buffer | Time 0 (%) | After 12 weeks (%) |
|---|---|---|---|
| Example 4 | Succinate | 16.6 | 22.5 |
| Comparative Example 1 | Phosphate | 16.7 | 25.1 |
| Comparative Example 2 | Histidine | 16.3 | 25.1 |
| Comparative Example 3 | Citrate | 16.7 | 22.6 |

As is apparent from the results of Table 4, the succinate buffer formulation (Example 4) exhibited superb stabilization effects in terms of aggregate formation compared to the phosphate buffer formulation (Comparative Example 1) and the histidine buffer formulation (Comparative Example 2). Also, the succinate buffer formulation (Example 4) manifested similar stabilization effects in terms of aggregate formation compared to the citrate buffer formulation (Comparative Example 3). Among the TNFR-Fc fusion protein formulations, the citrate buffer formulation is problematic in causing pain (U.S. Pat. No. 6,150,331 A, US 20110070231 A1), and thus the TNFR-Fc fusion protein formulation comprising succinate is preferable.

Therefore, the formulation comprising succinate was stable compared to conventional TNFR-Fc fusion protein formulations, and exhibited superior or similar stability compared to the other buffers.

2) Oxidation (M272) Analysis

In order to compare the oxidation inhibitory effects depending on the kind of buffer, the succinate-containing formulation (Example 4), the phosphate-containing formulation (Comparative Example 1), the histidine-containing formulation (Comparative Example 2) and the citrate-containing formulation (Comparative Example 3) were stored at 40° C. for 12 weeks, after which peptide mapping analysis was performed.

TABLE 5

| No. | Buffer | Time 0 (%) | After 12 weeks (%) |
|---|---|---|---|
| Example 4 | Succinate | 1.7 | 2.6 |
| Comparative Example 1 | Phosphate | 1.7 | 3.5 |
| Comparative Example 2 | Histidine | 1.6 | 3.0 |
| Comparative Example 3 | Citrate | 1.7 | 3.2 |

As is apparent from Table 5, the succinate-containing formulation (Example 4) exhibited an effect of inhibiting an increase in the extent of oxidation compared to the phosphate-, histidine-, and citrate-containing formulations (Comparative Examples 1 to 3).

Therefore, the succinate manifested high stabilization effects in terms of inhibiting the extent of oxidation of the TNFR-Fc fusion protein, compared to the stabilizer-containing phosphate, histidine and citrate buffers.

3. Test Example 3: Evaluation of Stability Depending on Succinate and Sodium Chloride Concentrations (1) SE-HPLC Analysis The stability of TNFR-Fc fusion protein was demonstrated by the succinate-containing formulation through Test Examples 1 and 2. In order to test the stabilization effect of the formulation depending on the succinate concentration, the 5 mM succinate formulation (Example 1), the 10 mM succinate formulation (Example 4) and the 25 mM succinate formulation (Example 2) were compared. Furthermore, in order to test the stabilization effect of the formulation depending on the NaCl concentration, the 120 mM NaCl formulation (Example 7), the 140 mM NaCl formulation (Example 4), and the 160 mM NaCl formulation (Example 8) were compared. Respective formulations were stored at 40° C. for 12 weeks, after which stability effects thereof were compared through SE-HPLC.

TABLE 6

| No. | Succinate concentration (mM) | NaCl concentration (mM) | After 12 weeks 40° C. (%) |
|---|---|---|---|
| Example 1 | 5 | 140 | 71.67 |
| Example 2 | 25 | 140 | 73.68 |
| Example 3 | 25 | 120 | 73.23 |
| Example 4 | 10 | 140 | 72.47 |
| Example 7 | 10 | 120 | 71.58 |
| Example 8 | 10 | 160 | 73.01 |

Table 6 shows the amounts of TNFR-Fc fusion protein (main peak), excluding impurities. In Examples 1, 4 and 2, comprising 140 mM NaCl and succinate at respective concentrations of 5 mM, 10 mM, and 25 mM, the amount of the TNFR-Fc fusion protein was increased in proportion to the succinate concentration.

Also, in Examples 7, 4 and 8, comprising 10 mM succinate and sodium chloride at respective concentrations of 120 mM, 140 mM, and 160 mM, the amount of the TNFR-Fc fusion protein was increased in proportion to the sodium chloride concentration.

Thereby, the stability of the TNFR-Fc fusion protein was further improved with an increase in the succinate content, and was outstanding in the presence of 25 mM succinate.

Also, the stability of the TNFR-Fc fusion protein was further improved with an increase in the sodium chloride content, and all of the formulations comprising sodium chloride at a concentration of 120 mM or more exhibited superior stabilization effects.

Moreover, the formulations comprising 25 mM succinate and 140 mM or more of sodium chloride manifested the most excellent stabilization effects.

(2) HI-HPLC Analysis

The HI-HPLC results were similar to the above SE-HPLC results of Test Example 3.

TABLE 7

| No. | Succinate concentration (mM) | NaCl concentration (mM) | After 12 weeks 40° C. (%) |
|---|---|---|---|
| Example 1 | 5 | 140 | 65.7 |
| Example 2 | 25 | 140 | 66.7 |
| Example 3 | 25 | 120 | 66.2 |
| Example 4 | 10 | 140 | 66.4 |
| Example 7 | 10 | 120 | 65.7 |
| Example 8 | 10 | 160 | 66.5 |

Table 7 shows the amounts of TNFR-Fc fusion protein, excluding impurities. In Examples 1, 4 and 2, comprising 140 mM NaCl and succinate at respective concentrations of 5 mM, 10 mM, and 25 mM, the amount of the TNFR-Fc fusion protein was increased in proportion to the succinate concentration. Also, in Examples 7, 4 and 8, comprising 10 mM succinate and sodium chloride at respective concentrations of 120 mM, 140 mM, and 160 mM, the amount of the TNFR-Fc fusion protein was increased in proportion to the sodium chloride concentration.

Thereby, the stability of the TNFR-Fc fusion protein was further improved with an increase in the succinate content, and was outstanding in the presence of 25 mM succinate.

Also, the stability of the TNFR-Fc fusion protein was further improved with an increase in the sodium chloride content, and all of the formulations comprising sodium chloride at a concentration of 120 mM or more exhibited superior stabilization effects.

Moreover, as is apparent from the results of Test Example 3, the formulations comprising 25 mM succinate and 140 mM or more of sodium chloride manifested the most excellent stabilization effects.

4. Test Example 4: Evaluation of Osmotic Pressure Depending on Sodium Chloride Concentration In order to evaluate the stability and osmotic pressure of the TNFR-Fc fusion protein depending on the sodium chloride concentration, the formulations of Examples 7, 4, and 8 were subjected to SE-HPLC analysis and osmotic pressure measurement. Respective formulations were stored at 40° C. for 12 weeks, after which SE-HPLC was performed and stability effects thereof were compared. Osmotic pressure was measured using a Wescor Vapro 5520 Vapor Pressure Osmometer. The results are shown in Table 8 below.

TABLE 8

| No. | NaCl concentration (mM) | After 12 weeks 40° C. (%) | Osmotic pressure (mOsm) |
|---|---|---|---|
| Example 7 | 120 | 71.58 | 241 |
| Example 4 | 140 | 72.47 | 280 |
| Example 8 | 160 | 73.01 | 333 |

Table 8 shows the results of osmotic pressure and amounts of TNFR-Fc fusion protein (main peak), excluding impurities, depending on the sodium chloride concentration. As set forth in Test Example 4, in Examples 7, 4 and 8, comprising 10 mM succinate and sodium chloride at respective concentrations of 120 mM, 140 mM, and 160 mM, the amount of the TNFR-Fc fusion protein was increased in proportion to the sodium chloride concentration. Furthermore, the osmotic pressure thereof was increased in proportion to the sodium chloride concentration.

As is typical in the art, a pharmaceutical formulation that is used as an injection in the human body is administered in the osmotic pressure range of 250 mOsm to 350 mOsm, similar to in-vivo osmotic pressure. In the case where a pharmaceutical formulation having an osmotic pressure falling outside of the above range is administered in the human body, pain may occur. Hence, based on the results of Test Example 4, the formulations comprising 120 to 160 mM sodium chloride exhibited excellent stabilization effects and osmosis effects.

5. Test Example 5: Evaluation of Stability Depending on pH of TNFR-Fc Fusion Protein Formulation Comprising Succinate Buffering Agent (1) SE-HPLC Analysis In order to evaluate the stabilization effect of a liquid formulation comprising succinate depending on pH, the pH 5.5 formulation (Example 5), the pH 6 formulation (Example 4), and the pH 6.5 formulation (Example 6), each of which comprises 10 mM succinate and 140 mM NaCl, were stored at 40° C. for 12 weeks and then subjected to SE-HPLC.

TABLE 9

| No. | pH | After 12 weeks 40° C. (%) |
|---|---|---|
| Example 5 | 5.5 | 66.13 |
| Example 4 | 6 | 72.47 |
| Example 6 | 6.5 | 71.87 |

As is apparent from Table 9, showing the amounts of TNFR-Fc fusion protein, excluding impurities, obtained through SE-HPLC, a superior stabilization effect at a pH of 6.0 resulted.

(2) HI-HPLC Analysis

Like the above SE-HPLC results of Test Example 5, similar results were exhibited in HI-HPLC.

TABLE 10

| No. | pH | After 12 weeks 40° C. (%) |
|---|---|---|
| Example 5 | 5.5 | 64.3 |
| Example 4 | 6 | 66.4 |
| Example 6 | 6.5 | 64.5 |

As is apparent from Table 10, showing the amounts of TNFR-Fc fusion protein, excluding impurities, obtained through HI-HPLC, a superior stabilization effect at a pH of 6.0 resulted.

What is claimed is:

1. A stable pharmaceutical formulation comprising:
   50 mg/ml of a fusion protein in which an extracellular ligand-binding domain of a human p75 tumor necrosis factor receptor is fused to an Fc domain of human IgG;
   an isotonic agent; and
   5-25 mM of succinate, without comprising a stabilizer, wherein the isotonic agent is sodium chloride at a concentration of 120 to 160 mM.

2. The stable pharmaceutical formulation of claim 1, wherein the formulation is free of an amino acid, an ammonium salt, a saccharide or a mixture thereof as a stabilizer.

3. The stable pharmaceutical formulation of claim 1, wherein the fusion protein comprises the amino acid sequence of SEQ ID NO:1.

4. The stable pharmaceutical formulation of claim 1, wherein the fusion protein comprises the amino acid sequence of SEQ ID NO:2.

5. The stable pharmaceutical formulation of claim 1, wherein the stable pharmaceutical formulation has a pH range from 5.5 to 6.5.

6. The stable pharmaceutical formulation of claim 2, wherein the ammonium salt is ammonium chloride, ammonium sulfate, ammonium carbonate, ammonium nitrate or a mixture thereof.

7. The stable pharmaceutical formulation of claim 2, wherein the amino acid is arginine, methionine, lysine, histidine, glycine, proline, alanine, valine, isoleucine, leucine, phenylalanine, tyrosine, tryptophan, cysteine, aspartic acid, glutamic acid, serine, asparagine, threonine, glutamine or a mixture thereof.

8. The stable pharmaceutical formulation of claim 2, wherein the saccharide is sucrose.

9. The stable pharmaceutical formulation of claim 1, wherein a high-molecular-weight component content is 12% or less, as measured using size-exclusion high-performance liquid chromatography (SE-HPLC) after storage at a temperature of 40° C.±2° C. for 12 weeks.

10. The stable pharmaceutical formulation of claim 1, wherein the high-molecular-weight component content is 24% or less, as measured using hydrophobic-interaction high-performance liquid chromatography (HI-HPLC) after storage at a temperature of 40° C.±2° C. for 12 weeks.

11. A kit comprising: a container comprising said formulation of claim 1 and instructions for administration of said formulation to a patient.

12. A method of producing a stable liquid pharmaceutical formulation comprising the steps of:
   (a) preparing 5-25 mM succinate buffer having a pH 5.5 to 6.5;
   (b) adding 50 mg/ml of a fusion protein in which an extracellular ligand-binding domain of a human p75 tumor necrosis factor receptor is fused to an Fc domain of human IgG to said buffer of step (a) to form a buffer/protein mixture; and
   (c) adding 120 to 160 mM of sodium chloride to said buffer/protein mixture of step (b) in order to form said stable liquid pharmaceutical formulation, wherein the formulation is free of a stabilizer, an amino acid, an ammonium salt, a saccharide, polysorbate, poloxamer, a polymer, or a mixture thereof.

13. The stable pharmaceutical formulation of claim 1, wherein the formulation comprises:
   a concentration of 50 mg/ml of the fusion protein;
   a concentration of 120 to 160 mM of sodium chloride as the isotonic agent;
   a concentration of 5-25 mM of succinate; and
   a pH range from 5.5 to 6.5;
   wherein the formulation is free of a stabilizer, an amino acid, an ammonium salt, a saccharide, polysorbate, poloxamer, a polymer, or a mixture thereof, and
   wherein a high-molecular-weight component content is 12% or less, as measured using size-exclusion high-performance liquid chromatography (SE-HPLC) after storage at a temperature of 40° C.±2° C. for 12 weeks.

* * * * *